United States Patent [19]

Lee et al.

[11] Patent Number: 4,552,598

[45] Date of Patent: Nov. 12, 1985

[54] ETHYLENEDIAMINE SALT OF 5-NITROTETRAZOLE AND PREPARATION

[75] Inventors: Kien-yin Lee; Michael D. Coburn, both of Los Alamos, N. Mex.

[73] Assignee: The United States of America as represented by the United States Department of Energy, Washington, D.C.

[21] Appl. No.: 611,557

[22] Filed: May 17, 1984

[51] Int. Cl.$^4$ .............................................. C06B 31/32
[52] U.S. Cl. ........................................ 149/47; 149/92; 149/109.6; 548/109; 548/251
[58] Field of Search .................. 149/47, 92, 109.6; 548/109, 251

[56] References Cited

U.S. PATENT DOCUMENTS 4,093,623 6/1978 Gilligan et al. .................. 548/109
4,094,879 6/1978 Bates et al. ....................... 548/109
4,300,962 11/1981 Stinecipher ........................ 149/47

Primary Examiner—Stephen J. Lechert, Jr.
Attorney, Agent, or Firm—Samuel M. Freund; Paul D. Gaetjens; Judson R. Hightower

[57] ABSTRACT

Ethylenediamine salt of 5-nitrotetrazole and preparation. This salt has been found to be useful as an explosive alone and in eutectic mixtures with ammonium nitrate and/or other explosive compounds. Its eutectic with ammonium nitrate has been demonstrated to behave in a similar manner to a monomolecular explosive such as TNT, and is less sensitive than the pure salt. Moreover, this eutectic mixture, which contains 87.8 mol % of ammonium nitrate, is close to the $CO_2$-balanced composition of 90 mol %, and has a relatively low melting point of 110.5 C. making it readily castable. The ternary eutectic system containing the ethylenediamine salt of 5-nitrotetrazole, ammonium nitrate and ethylenediamine dinitrate has a eutectic temperature of 89.5 C. and gives a measured detonation pressure of 24.8 GPa, which is 97.6% of the calculated value. Both the pure ethylenediamine salt and its known eutectic compounds behave in substantially ideal manner. Methods for the preparation of the salt are described.

38 Claims, No Drawings

ETHYLENEDIAMINE SALT OF 5-NITROTETRAZOLE AND PREPARATION

This invention is the result of a contract with the Department of Energy (Contract No. W-7405-ENG-36).

BACKGROUND OF THE INVENTION

The present invention relates generally to explosive compositions, and more particularly to the ethylenediamine salt of 5-nitrotetrazole and mixtures thereof.

Ammonium nitrate is an inexpensive and readily available oxidizer used extensively in commercial explosives. Unfortunately, one of the disadvantages of this material which limits its utility for military explosives is its nonideal behavior. Generally, detonation pressures and velocities are lower which results in lower power output for nonideal explosives when compared to ideal explosives. Over the past ten years, attempts have been made to obtain ideal explosive behaviour from composites of ammonium nitrate with various fuels. The most promising of these investigations has involved the formation of low-melting eutectic mixtures of the fuel under investigation and ammonium nitrate. The eutectics offer the advantage of being readily castable for military applications. Moreover, the intimate mixing of the component substances which results when eutectic mixtures are cooled below their melting temperatures offers the best opportunity for obtaining close to ideal performance. That is, the fuel and the ammonium nitrate oxidizer interact and detonate as a single component rather than as individual components.

The ammonium salt of 3,5-dinitro-1,2,4-triazole was found to form a low-melting eutectic with ammonium nitrate that was subsequently shown to perform as a near ideal explosive. Indeed, eutectic compositions involving ammonium nitrate and ammonium salts of several nitroheterocycles have been described in U.S. Pat. No. 4,300,962 "Ammonium Nitrate Explosive Systems," issued to Mary M. Stinecipher and Michael D. Coburn. However, the ammonium salt of 3,5-dinitro-1,2,4-triazole performed best as an explosive. This discovery was the basis for searching for a more efficient and less hazardous procedure for producing this compound which is the subject of U.S. Pat. No. 4,236,014. "Production of the Ammonium Salt of 3,5-dinitro-1,2,4-triazole by Solvent Extraction," issued to Kien-yin Lee and Donald G. Ott on Nov. 25, 1980. Neither of the above-described patents teaches the use of the ethylenediamine salt of 5-nitrotetrazole as the fuel in an ammonium nitrate eutectic or the preparation of this material. The former patent does mention the ammonium salt of 5-nitrotetrazole and its preparation, however. The finding that ammonium based mixtures could be made which exhibited near-ideal explosive performance further encouraged the search for other, less expensive materials that would form similar eutectics or solid solutions with ammonium nitrate, which search led to the subject invention.

W. H. Gilligan and M. J. Kamlet describe the preparation of metallic salts of 5-nitrotetrazole in "Synthesis of Mercuric-5-nitrotetrazole," Naval Surface Weapons Center Report NSWC/WOL/TR 76-146, Dec. 1976. However, their procedure involves the step of isolating the extremely sensitive copper salt of 5-nitrotetrazole. The subject process eliminates this hazardous step and demonstrates a one-pot process for obtaining a solution of the insensitive sodium salt as precursor to the organic salts of interest.

SUMMARY OF THE INVENTION

Accordingly, it is an object of the present invention to provide a new explosive composition of matter which behaves in a substantially ideal manner.

Another object of this invention is to provide a new castable explosive mixture which behaves in a substantially ideal manner.

Yet another object of our invention is to provide an efficient and less hazardous method for the preparation of the ethylenediamine salt of 5-nitrotetrazole.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed in the appended claims.

To achieve the foregoing and other objects, in accordance with the purposes of the present invention, as embodied and broadly described herein, the explosive composition of matter hereof includes the ethylenediamine salt of 5-nitrotetrazole.

In a further aspect of this invention, in accordance with its objects and purposes, the explosive mixture hereof includes ammonium nitrate and the ethylenediamine salt of 5-nitrotetrazole. Preferably, the explosive mixture is a eutectic mixture having about 87.5 mol% of ammonium nitrate.

In a further aspect of the subject invention, in accordance with its objects and purposes, the explosive mixture hereof includes ammonium nitrate, the ethylenediamine salt of 5-nitrotetrazole and ethylenediamine dinitrate. Preferably, the explosive mixture is a eutectic having a eutectic melting temperature of approximately 89.5 C.

In yet a further aspect of the present invention, in accordance with its objects and purposes, the method hereof for preparing the ethylenediamine salt of 5-nitrotetrazole includes forming a first aqueous solution which includes cupric sulfate and an excess of sodium nitrite, forming a second aqueous solution which includes 5-aminotetrazole, cupric sulfate and sulfuric acid, maintaining said second solution in a cooled state while said first solution is added dropwise thereto forming thereby a third solution, stirring the third solution for about 1 hour at room temperature, adjusting the pH of the third solution to approximately 9.5 using a solution of sodium hydroxide, forming thereby a fourth solution, heating the fourth solution to about 70 C. for about 1 hour, whereby the copper salt of 5-nitrotetrazole is converted to the sodium salt thereof with the simultaneous precipitation of cupric oxide from the solution, removing the cupric oxide precipitate, acidifying the fourth solution using sulfuric acid forming thereby a fifth solution, extracting the fifth solution with trilaurylamine dissolved in dichloroethane, forming thereby an organic extract, treating the organic extract with anhydrous ammonia producing thereby an ammonium salt precipitate, collecting the ammonium salt precipitate, washing the ammonium salt precipitate with dichloroethane, drying the washed precipitate, dissolving the washed precipitate in methanol forming thereby a sixth solution, adding ethylenediamine to the sixth solution initiating thereby a chemical reaction which yields the ethylenediamine salt of 5-nitrotetrazole, waiting a sufficient time period for the reaction to proceed to substantial completion, and removing the methanol. Preferably, the dried ammonium salt is stirred with methanol and filtered and the resulting filtrate evaporated to dryness in order to remove trace amounts of inorganic sulfate before the chemical reaction step with the ethylenediamine. Preferably also, the ethylenediamine salt of 5-nitrotetrazole is recrystallized from a water/methanol solution to increase its purity.

In still a further aspect of our invention, in accordance with its objects and purposes, the method hereof for preparing the ethylenediamine salt of 5-nitrotetrazole includes forming a first aqueous solution which includes cupric sulfate and an excess of sodium nitrite, forming a second aqueous solution which includes 5-aminotetrazole, cupric sulfate and sulfuric acid, maintaining said second solution in a cooled state while said first solution is added to dropwise thereto forming thereby a third solution, stirring the third solution for about one hour at room temperature, adjusting the pH of the third solution to approximately 9.5 using a solution of sodium hydroxide, forming thereby a fourth solution, heating the fourth solution to about 70 C. for about one hour, whereby the copper salt of 5-nitrotetrazole is converted to the sodium salt thereof with the simultaneous precipitation of cupric oxide from the solution, removing the cupric oxide precipitate, acidifying the fourth solution using sulfuric acid forming thereby a fifth solution, extracting the fifth solution with trilaurylamine dissolved in dichloroethane, forming thereby an organic extract, treating the organic extract with ethylenediamine producing thereby the ethylenediamine salt of 5-nitrotetrazole as a precipitate, collecting the ethylenediamine salt precipitate, washing the ethylenediamine salt precipitate with dichloroethane, and drying the ethylenediamine salt precipitate. Preferably, the ethylenediamine salt of 5-nitrotetrazole is recrystallized from a water/methanol solution to increase its purity.

In another aspect of the instant invention, in accordance with its objects and purposes, the method hereof for preparing the ethylenediamine salt of 5-nitrotetrazole includes dissolving ammonium 5-nitrotetrazole in methanol forming thereby a first solution, adding ethylenediamine to the first solution, forming thereby a second solution, waiting a sufficient time period for substantial reaction to occur between the ammonium 5-nitrotetrazole and the ethylenediamine, and removing the methanol solvent. Preferably, the ethylenediamine salt of 5-nitrotetrazole is purified by recrystallizing the salt from a water/methanol mixture.

In summary, the subject invention includes the discovery of a new, inexpensive and simply prepared explosive and eutectic mixtures thereof with ammonium nitrate and/or ethylenediamine dinitrate, all of which exhibit near ideal explosive behavior. The simplified preparation procedures of our invention substantially reduce the risks associated with the synthesis of this composition of matter. Additionally, the eutectic composition of the ethylenediamine salt of 5-nitrotetrazole and ammonium nitrate lies close to the $CO_2$-balanced composition of 90 mol% of ammonium nitrate offering thereby a formulation which is both $CO_2$-balanced and has a relatively low melting point which improves its castability.

DETAILED DESCRIPTION OF THE INVENTION

Reference will now be made in detail to the present preferred embodiments of the invention, which are illustrated in the accompanying examples.

Turning now to the preparation of the ethylenediamine salt of 5-nitrotetrazole, two processes have been found to be useful. In both of these preparations, the hazardous step of isolating the extremely sensitive copper salt of 5-nitrotetrazole has been eliminated and a one-pot process has been developed for obtaining a solution of the insensitive sodium salt.

EXAMPLE I

To a stirred solution of sodium nitrite (104 g, 1.5 mol), cupric sulfate (55 g, 0.22 mol) in 300 ml water, a solution of 5-aminotetrazole (51.5 g, 0.5 mol), cupric sulfate (2 g, 0.008 mol) and concentrated sulfuric acid (51.0 g, 0.5 mol) in 700 ml water at 10–15 C. was added dropwise. After stirring at room temperature for one hour, the resulting mixture was adjusted to pH 9.5 with 50% sodium hydroxide and heated at 70 C. for one hour to convert the copper salt of 5-nitrotetrazole to the sodium salt and cupric oxide according to reaction (1).

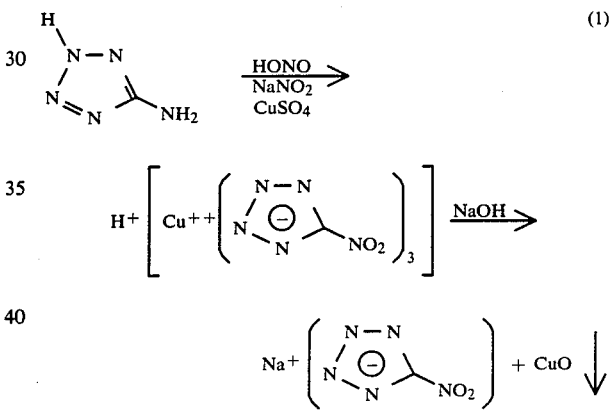

(1)

The precipitated cupric oxide was removed by filtration, and the yield of sodium salt was determined to be 96% by spectrophotometry at 255 nm. The sodium salt solution was acidified with an equivalent amount of concentrated sulfuric acid and extracted with trilaurylamine (Alamine 304, $R_3N$) in dichloroethane. The organic extract was dried with magnesium sulfate and treated with anhydrous ammonia. The precipitated ammonium salt was collected by filtration, washed several times with dichloroethane, and dried to yield 53.5 g (81%) according to reaction (2).

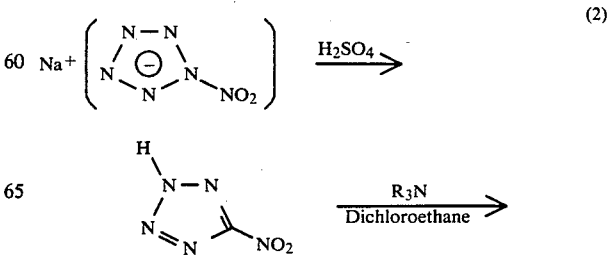

(2)

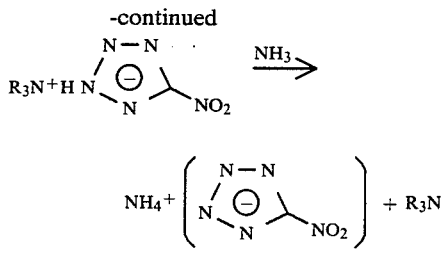

To remove trace amounts of inorganic sulfate, the solid product was stirred with methanol (250 ml) and filtered. The filtrate was evaporated to dryness to yield the pure ammonium salt. The purity was determined by the ammonia ion-selective-electrode method to be 99.8%. The ethylenediamine salt of 5-nitrotetrazole can then be prepared by addition of one equivalent of ethylenediamine to a methanol solution of two equivalents of the ammonium salt, followed by evaporation of the solvent according to reaction (3).

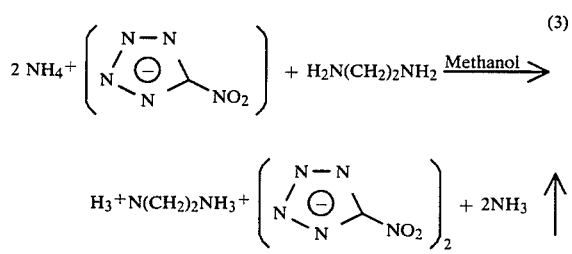

The yield of pure ethylenediamine salt by this method is 85%. NMR analysis showed the product salt to be free of impurities. The ethylenediamine salt can be readily recrystallized from a water/methanol solution.

EXAMPLE II

If ethylenediamine is used instead of ammonia in the last step of Reaction 2, the ethylenediamine salt of 5-nitrotetrazole will be the final product.

The salt is soluble in water and methanol and insoluble in other common organic solvents. The physical and explosive properties of the ethylenediamine salt of the instant invention are listed in Table I. Results of the small-scale sensitivity tests of $CO_2$-balanced mixtures of ammonium nitrate and the ethylenediamine salt of 5-nitrotetrazole are also given in Table I. These mixtures were prepared by melting the mixed components together in a beaker that was heated by an oil bath. The molten mixture was poured quickly and spread evenly onto a sheet of Teflon to solidify. The $CO_2$-balanced mixture, which also closely approximates a eutectic mixture, was found to be less sensitive to impact and sparks than the pure fuel component, the ethylenediamine salt of 5-nitrotetrazole. Note that the vacuum stability of the binary eutectic mixture is only 0.2 ml/g/48 h at 100 C., even though it is 2.4 ml/g/48 h at 120 C. As best understood by the inventors, the large number for this quantity is not an indication of incompatibility between the ethylenediamine salt and ammonium nitrate because the mixture is a liquid at 120 C. and the ethylenediamine salt is a solid at this temperature. The vacuum stability of the eutectic mixture is good at 100 C., where both the salt and the eutectic mixture are solid.

TABLE I

| | Pure Compound (Ethylenediamine Salt of 5-Nitrotetrazole) | Eutectic Mixture Of The Ethylenediamine Salt Of 5-Nitro- tetrazole With Ammonium Nitrate |
|---|---|---|
| Formula: | $C_4H_{10}N_{12}O_4$ | |
| Crystal Density: | 1.65 g/cm$^3$ | |
| Melting Point: | 221 C. | 110.5 |
| DTA: | Stable to 216 C. | 200 |
| Vacuum Stability | | |
| (ml/g/48 h at 120 C.): | 0.5 | 2.4 |
| (ml/g/48 h at 100 C.) | | 0.2 |
| Impact Sensitivity | | |
| (Type 12): | 42 cm | 78.8 |
| (Type 12B): | 51 | 264 |
| Heat of Formation ($\Delta H_f$): | +55.7 kcal/mole | |
| Spark Sensitivity | | |
| (3 mil foil): | 1.70 J | 2.30 |
| (10 mil foil): | 4.70 | 6.38 |
| Henkin Critical Temperature: | 208 C. | 234 |
| C-J Pressure: | 23.7 GPa | 19.2 |
| Detonation Velocity (calc): | 7,020 m/s | 7780 |
| Analysis for $C_4H_{10}N_{12}O_4$: | | |
| Theory: | C, 16.54; H, 3.45; N, 57.91 | |
| Found: | C, 16.51; H, 3.61; N, 58.27. | |

In addition, accelerating rate calorimetry shows that the mixtures are stable below 160 C. and that the thermal decomposition occurs slowly over a long period of time.

The salt forms a eutectic with ammonium nitrate which melts at 110.5 C. The eutectic composition is 87.8 mol% ammonium nitrate (66.5 wt% ammonium nitrate). This eutectic composition is close to the $CO_2$-balanced composition of 90 mol% ammonium nitrate. Therefore, it becomes very attractive from the economic viewpoint of utilizing the greatest amount of inexpensive ammonium nitrate in a $CO_2$-balanced composition. Moreover, the $CO_2$-balanced eutectic formulation offers the processing advantages of being close to the eutectic composition and having a relatively low melting point.

Stock samples for phase-diagram determination were prepared by weighing and then mixing the appropriate amounts of salts with a mortar and pestle. The mixture was ground in the presence of a small amount of methanol and evaporated to dryness to ensure homogeneous mixing. Slides were prepared for phase-transition observation by melting a small amount of the stock sample mixture on a slide, then cooling it immediately to room temperature. A Carl Zeiss microscope, equipped with a Mettler instrument AG Model FP-2 hot stage accurate to 0.3 C., was used to observe phase transition.

When the ethylenediamine salt of our invention is mixed with ammonium nitrate and ethylenediamine dinitrate, the eutectic melt temperature is lowered, and the grain size of the final melt is finer than that of the binary ethylenediamine dinitrate mixture. The eutectic composition of the ammonium nitrate/ethylenediamine dinitrate/ethylenediamine salt of 5-nitrotetrazole system is 72/17/11 mol % (47.54/26.13/26.33 wt%), respectively, and the eutectic temperature is 89.5 C.

Mixtures of both ammonium nitrate/ethylenediamine salt of 5-nitrotetrazole and ammonium nitrate/ethylenediamine dinitrate/ethylenediamine salt of 5-nitrotetrazole were subjected to small-scale sensitivity tests and unconfined plate-dent tests. The results of these tests are reported in Table II. The detonation velocities of the formulations were determined with 2.54-cm-diameter unconfined rate sticks. The results of the detonation velocity measurements of $CO_2$-balanced eutectics are compared with the predicted values calculated by the Kamlet-Jacobs method (KSM) assuming ideal behavior. The measured velocities of both systems are within 95% of those calculated by the Kamlet-Jacobs method. It is believed by the inventors the results may be somewhat lower than predicted because the tests may have been conducted near the failure diameters of the eutectics.

The subject invention then includes the discovery of a new explosive and explosive eutectic mixtures thereof all of which behave in a near-ideal manner. Two methods of preparation for the explosive are described which derive from readily obtainable reagents and are relatively safe.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated.

TABLE II

| Explosive System | Density $(g/cm^3)$ | Impact Sensitivity (Type 12) | Dent (mm) | $P_{C-J}$ (GPa) | $P_{C-J}$ KSM | Velocity (m/s) | Velocity KSM |
|---|---|---|---|---|---|---|---|
| ammonium nitrate/ethylenediamine salt of 5-nitrotetrazole (66.5 wt % ammonium nitrate) | 1.568 | 78.8 | 3.38 | 19.2 | 24.8 | 7400.0 | 7780.0 |
| ammonium nitrate/ethylenediamine dinitrate/ ethylenediamine salt of 5-nitrotetrazole (47.54/26.13/26.33 wt. %) | 1.618 | 98.6 | 7.14 | 24.8 | 25.41 | — | 7818.0 |

It is intended that the scope of the invention be defined by the claims appended hereto.

What we claim is:

1. A process for preparing the ethylenediamine salt of 5-nitrotetrazole, which comprises the steps of:
   a. dissolving two equivalents of ammonium 5-nitrotetrazole in methanol forming thereby a first solution;
   b. adding one equivalent of ethylenediamine to said first solution, forming thereby a second solution;
   c. allowing sufficient interaction time to permit said ammonium 5-nitrotetrazole and said ethylenediamine in said second solution to react to substantial completion; and
   d. removing said methanol.
2. The process as described in claim 1, wherein the ethylenediamine salt of 5-nitrotetrazole is purified by adding to the steps of dissolving the ethylenediamine salt in methanol and recrystallizing the ethylenediamine salt therefrom.
3. The process as described in claim 1, wherein the ethylenediamine salt of 5-nitrotetrazole is purified by adding the steps of dissolving the ethylenediamine salt in water and recrystallizing the ethylenediamine salt therefrom.
4. The process as described in claim 1, wherein the ethylenediamine salt of 5-nitrotetrazole is purified by adding the steps of dissolving the ethylenediamine salt in a mixture of methanol and water and recrystallizing the ethylenediamine salt therefrom.
5. A process for preparing the ethylenediamine salt of 5-nitrotetrazole, which consists essentially of the steps of:
   a. dissolving two equivalents of ammonium 5-nitrotetrazole in methanol forming thereby a first solution;
   b. adding one equivalent of ethylenediamine to said first solution, forming thereby a second solution;
   c. allowing sufficient interaction time to permit said ammonium 5-nitrotetrazole and said ethylenediamine in said second solution to react to substantial completion; and
   d. removing said methanol.
6. The process as described in claim 5, wherein the ethylenediamine salt of 5-nitrotetrazole is purified by adding the steps of dissolving the ethylenediamine salt in a mixture of methanol and water and recrystallizing the ethylenediamine salt therefrom.
7. An explosive composition of matter which comprises the ethylenediamine salt of 5-nitrotetrazole.
8. An explosive composition of matter which consists essentially of the ethylenediamine salt of 5-nitrotetrazole.
9. An explosive composition of matter which comprises a mixture of the ethylenediamine salt of 5-nitrotetrazole and ammonium mixture.
10. The explosive composition of matter as described in claim 9, wherein said mixture is $CO_2$ balanced.
11. The explosive composition of matter as described in claim 10, wherein said mixture is a eutectic mixture having a eutectic melting temperature of about 110.5 C.
12. The explosive composition of matter as described in claim 11, wherein said ammonium nitrate has a concentration of approximately 87.5 mol%.
13. An explosive composition of matter which consists essentially of a mixture of the ethylenediamine salt of 5-nitrotetrazole and ammonium nitrate.
14. The explosive composition of matter as described in claim 13, wherein said mixture is $CO_2$ balanced.
15. The explosive composition of matter as described in claim 14, wherein said mixture is a eutectic mixture having a eutectic melting temperature of about 110.5 C.
16. The explosive composition of matter as described in claim 15, wherein said ammonium nitrate has a concentration of approximately 87.5 mol%.
17. An explosive composition of matter which comprises a mixture of the ethylenediamine salt of 5- nitrotetrazole, ammonium nitrate and ethylenediamine dinitrate.

18. The explosive composition of matter as described in claim 17, wherein said mixture is a eutectic mixture having a eutectic melting temperature of about 89.5 C.

19. An explosive composition of matter which consists essentially of a mixture of the ethylenediamine salt of 5-nitrotetrazole, ammonium nitrate and ethylenediamine dinitrate.

20. The explosive composition as described in claim 19, wherein said mixture is a eutectic mixture having a eutectic melting temperature of about 89.5 C.

21. A process for preparing the ethylenediamine salt of 5-nitrotetrazole, which comprises the steps of:
  a. dissolving sodium nitrite and cupric sulfate in water, forming thereby a first solution:
  b. dissolving 5-aminotetrazole, cupric sulfate and sulfuric acid in water, forming thereby a second solution;
  c. adding said second solution to said first solution, forming thereby a third solution;
  d. basifying said third solution using a solution of sodium hydroxide, forming thereby a fourth solution;
  e. heating said fourth solution, whereby the copper salt of 5-nitrotetrazole is converted to the sodium salt thereof, and whereby cupric oxide is simultaneously formed and precipitates from said fourth solution;
  f. removing said precipitated cupric oxide;
  g. acidifying said fourth solution using an equivalent amount of sulfuric acid, forming thereby a fifth solution;
  h. extracting said fifth solution using at least one water-insoluble amine dissolved in an organic diluent in which said 5-nitrotetrazole is also soluble, while the ammonium salt of 5-nitrotetrazole precipitates therefrom, producing thereby an organic extract;
  i. drying said organic extract;
  j. treating said organic extract with anhydrous ammonia producing thereby an ammonium salt precipitate;
  k. collecting said ammonium salt precipitate;
  l. dissolving two equivalents of said dried ammonium salt precipitate in methanol forming thereby a sixth solution;
  m. adding one equivalent of ethylenediamine to said sixth solution initiating thereby a chemical reaction;
  n. waiting a sufficient amount of time for said chemical reaction to go to substantial completion; and
  o. removing said methanol.

22. The process as described in claim 21, wherein said at least one water-insoluble amine for extracting said fifth solution includes trilaurylamine.

23. The process as described in claim 22, wherein said organic diluent includes dichloroethane.

24. The process as described in claim 23, wherein said ammonium salt precipitate is washed with dichloroethane and then dried, producing thereby a first purified ammonium salt precipitate, said first purified ammonium salt precipitate subsequently being stirred with methanol and filtered, and the resulting filtrate evaporated to dryness in order to remove trace amounts of inorganic sulfate, forming thereby a second purified ammonium salt precipitate before performing said step of forming said sixth solution.

25. The process as described in claim 24, wherein said step of dissolving said sodium nitrite includes dissolving an excess of sodium nitrite.

26. The process as described in claim 25, wherein said dissolving of said 5-aminotetrazole, cupric sulfate and sulfuric acid in water to form said second solution is performed with said water being held between about 10 and 15 C.

27. The process as described in claim 26, wherein said basifying of said third solution step is performed such that the final pH of said fourth solution is approximately 9.5.

28. The process as described in claim 27, wherein said fourth solution is heated to approximately 70 C. for about one hour.

29. The process as described in claim 28, wherein said third solution is stirred for approximately one hour and held at about room temperature.

30. A process for preparing the ethylenediamine salt of 5-nitrotetrazole, which comprises the steps of:
  a. dissolving sodium nitrite and cupric sulfate in water, forming thereby a first solution:
  b. dissolving 5-aminotetrazole, cupric sulfate and sulfuric acid in water, forming thereby a second solution;
  c. adding said second solution to said first solution, forming thereby a third solution;
  d. basifying said third solution using a solution of sodium hydroxide, forming thereby a fourth solution;
  e. heating said fourth solution, whereby the copper salt of 5-nitrotetrazole is converted to the sodium salt thereof, and whereby cupric oxide is simultaneously formed and precipitates from said fourth solution;
  f. removing said precipitated cupric oxide:
  g. acidifying said fourth solution using an equivalent amount of sulfuric acid, forming thereby a fifth solution;
  h. extracting said fifth solution using at least one water-insoluble amine dissolved in an organic diluent in which said 5-nitrotetrazole is also soluble, while the ethylenediamine salt of 5-nitrotetrazole precipitates therefrom, producing thereby an organic extract;
  i. drying said organic extract;
  j. treating said organic extract with ethylendiamine producing thereby an ethylenediamine salt precipitate; and
  k. collecting said ethylenediamine salt precipitate.

31. The process as described in claim 30, wherein said at least one water-insoluble amine for extracting said fifth solution includes trilaurylamine.

32. The process as described in claim 31, wherein said organic diluent includes dichloroethane.

33. The process as described in claim 32, wherein said step of dissolving said sodium nitrite includes dissolving an excess of sodium nitrite.

34. The process as described in claim 33, wherein said dissolving of said 5-aminotetrazole, cupric sulfate and sulfuric acid in water to form said second solution is performed with said water being held between about 10 and 15 C.

35. The process as described in claim 34, wherein said basifying of said third solution step is performed such that the final pH of said fourth solution is approximately 9.5.

36. The process as described in claim 35, wherein said fourth solution is heated to approximately 70 C. for about one hour.

37. The process as described in claim 36, wherein said third solution is stirred for approximately one hour and held at about room temperature.

38. The process as described in claim 37, wherein said dried ethylenediamine salt precipitate is stirred with methanol and filtered, and the resulting filtrate evaporated to dryness in order to remove trace amounts of sulfate impurities.

* * * * *